United States Patent

Chung-Bong-Chan et al.

[11] Patent Number: 4,695,285
[45] Date of Patent: Sep. 22, 1987

[54] PROCESS FOR COLORING KERATINACEOUS MATERIALS

[75] Inventors: Alexander Chung-Bong-Chan, Mineola, N.Y.; Leszek J. Wolfram, Stamford, Conn.

[73] Assignee: Clairol Incorporated, New York, N.Y.

[21] Appl. No.: 919,174

[22] Filed: Oct. 15, 1986

[51] Int. Cl.$^4$ .................. A61K 7/13; A61K 7/42; D06P 5/20
[52] U.S. Cl. .................................. 8/429; 8/404; 8/405; 8/407; 8/444; 260/349; 424/59
[58] Field of Search .................. 260/349; 8/404, 405, 8/406, 429, 416, 408, 409, 421, 424, 444; 424/59

[56] References Cited

U.S. PATENT DOCUMENTS

| | | | |
|---|---|---|---|
| 3,062,650 | 11/1962 | Sagura et al. | 430/196 |
| 3,769,294 | 10/1973 | Catino et al. | 424/59 |
| 3,933,497 | 1/1976 | Singh | 260/349 |
| 4,019,907 | 4/1977 | Tsunoda et al. | 260/349 |
| 4,228,151 | 10/1980 | Lang et al. | 424/59 |
| 4,293,542 | 10/1981 | Lang et al. | 424/60 |
| 4,415,332 | 11/1983 | Lenox et al. | 8/444 |
| 4,556,625 | 12/1985 | Lenox et al. | 8/444 |

OTHER PUBLICATIONS

Milligan, et al., "Photoreactive Dyes: the Potential of Azido-Substituted Dyes as Latent Reactive Dyes for Wool", *Chemical Abstracts*, 90:24760g, 1979.
Griffiths, et al., "New Fiber-Reactive Dyes for Hydrophobic Fibers", *Chemical Abstracts*, 78:45020h, 1973.
Griffiths, et al., "Azide Reactive Dyes, Part II, Transfer-Printing Properties of Sulfonyl- and Aryl-Azide Dyes on Nylon 66, *Chemical Abstracts*, 89:7476f, 1978.
Ayyanger, et al., "Azides, Part I, Reactive Dyes Containing the Azido Group for Synthetic-Polymer Fibers", *Chemical Abstracts*, 90:139045y, 1979.

*Primary Examiner*—Paul Lieberman
*Assistant Examiner*—Linda D. Skaling
*Attorney, Agent, or Firm*—Gabriel P. Katona

[57] ABSTRACT

A process for dyeing keratinaceous substances such as hair, wool, skin etc., which comprises contacting the same with a composition containing an aromatic azide or azidoindole component having the formula

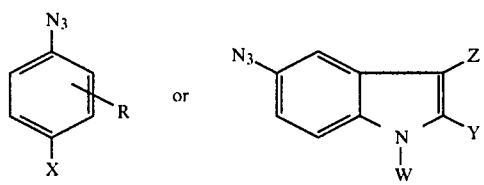

wherein X is hydroxyl, alkoxyl, NR'R", in which R' and R" are independently of each other hydrogen, alkyl or hydroxyalkyl, and if R' is H or alkyl, then R" can be further carbamylalkyl, mesylaminoalkyl, acylaminoalkyl, sulfoalkyl, piperidinoalkyl or morpholinoalkyl, R' and R" can also form with the nitrogen atom to which they are attached a piperidine or morpholine ring, R is hydrogen, alkyl, hydroxyalkyl, halogen, nitro, cyano or alkoxyl, W, Y and Z are independently of each other H or R', wherein all of the aforementioned alkyl moieties can have between 1 and 8 carbon atoms, and then exposing the contacted keratinaceous material to a suitable light source for sufficient time to develop the color. The composition can optionally also contain a color coupler component capable of interacting with said aromatic azide or azidoindole.

12 Claims, No Drawings

PROCESS FOR COLORING KERATINACEOUS MATERIALS

This invention relates to a process for coloring keratinaceous materials, e.g. hair, wool or skin. More particularly, it concerns a process of this type that relies on sunlight or other suitable light source for development of the color.

The conventional process for "permanently" coloring keratin fibers has generally involved contacting the fiber with a solution containing an oxidation dye system (e.g. p-phenylenediamine or p-phenylenediamine plus a color coupler). In such a process a large excess of aqueous hydrogen peroxide ($H_2O_2$) is employed in developing the color in the fiber. This kind of process has the disadvantage in that the hydrogen peroxide it employs tends to damage the fiber. The process of the present invention seeks to minimize this damage by eliminating the need for using hydrogen peroxide for color developing and by substituting therefore a suitable light source.

It has been found that keratinaceous material, for example, skin, wool or hair may be conveniently colored by treating it with a composition containing one or more aromatic azides with or without one or more color couplers or modifiers and then exposing the keratinaceous material so treated to a source of light for sufficient time to color said keratinaceous material. In a preferred manner for practicing the present invention the combination of the one or more aromatic azides with or without one or more color couplers or modifiers are applied to the keratinaceous material from an aqueous solution and allowed to penetrate into the same. The excess solution is then preferably rinsed or wiped off and the treated keratinaceous material is subjected to the action of a suitable light source for sufficient time to develop the color. Alternatively, the keratineous fibers can be dyed by applying the above solution to the fiber and exposing to a suitable light source simultaneously for sufficient time.

It is known in the prior art that skin can be colored by applying a number of different components to it and subjecting it to the action of the sun. These are exemplified by the U.S. Pat. No. 2,948,657 (Siccama, et al); U.S. Pat. No. 4,228,151 (Lang, et al) and U.S. Pat. No. 4,293,542 (Lang, et al). These references, however, do not teach the use of a aromatic azide and an optional color coupler or modifier as is characteristic of the process of the present invention, before exposing it to a suitable light source.

It is also known in the prior art to dye hair with autoxidizable hair dye systems that rely on atmospheric oxygen to develop their color. References of this character are illustrated by U.S. Pat. No. 3,134,721 (Seemuller) and U.S. Pat. No. 3,184,387 (Seemuller). However, as with the other references discussed above these processes do not employ an aromatic azide alone or in combination with one or more selected couplers as in the case of the present invention.

U.S. Pat. No. 4,415,332 (Lenox, et al) is of interest in disclosing a process for photolytically developing color on a polyamide textile fiber. The textile fibers that this reference has in mind is nylon. The coloring agent used in this reference is an aminobenzenesulfonylazide which is characterized by the fact that the functional group

is bonded to a benzene ring carbon atom. The process at this reference differs from that of the present invention in several important respects. In the first place it is concerned with the coloring of polyamide fibers, like nylon, and not skin, wool or hair with which the present invention is concerned. Furthermore, the coloring agent used in this reference is significantly different chemically from that employed in the present invention in that the azide group ($N_3-$) is bonded to the benzene carbon atom through a sulfonyl group. This is to be distinguished from the azide employed in the present invention in which the azide group ($N_3-$) is bonded directly to a ringcarbon atom. Moreover, the process of the present invention may also employ a color coupler which is not employed in the process of Lenox, et al.

U.S. Pat. No. 3,062,650 relates to photographic reproduction methods in which phenylazides and couplers are "incorporated in a self-supporting layer". Print-out images can be obtained by exposing this layer to a light source. This process differs from that of the present invention in that it concerns a photographic process and not the coloring of keratinaceous material as is characteristic of the process of this invention. Photographic processes are known to have very different chemical requirements from keratinaceous material coloring.

The self-supporting layer of U.S. Pat. No. 3,062,650 is quite different physically from the keratinaceous material that is treated in accordance with the present invention. The treatment of the present invention requires that the dye composition be allowed to penetrate the keratinaceous material either before or while it is subjected to the action of a suitable light source. Secondly, in the process of this invention the dye solution applied to the keratinaceous material preferably be rinsed off before exposing the keratinaceous material to the action of the light source. There is no corresponding step or steps in the photographic process of U.S. Pat. No. 3,062,650.

The aromatic azides that may be used to practice the process of the present invention are quite varied. Generally, these may be described as phenylazides or azidoindoles of the general formula:

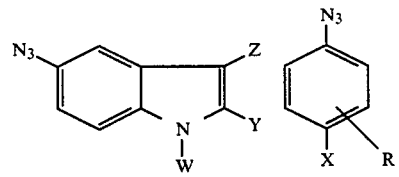

wherein X is hydroxyl, alkoxyl, NR'R", in which R' and R" are independently of each other hydrogen, alkyl or hydroxyalkyl, and if R' is H or alkyl, then R" can be further carbamylalkyl, mesylaminoalkyl, acylaminoalkyl, sulfoalkyl, piperidinoalkyl or morpholinoalkyl, R' and R" can also form, together with the nitrogen atom to which they are attached, a piperidine or morpholine ring. The radical R denotes H, alkyl, hydroxyalkyl, halogen, nitro, cyano or alkoxyl, W, Y and Z are independently of each other H or R', wherein all of the aforementioned alkyl moieties can have independently of each other between 1 and 8 carbon atoms.

In practicing the process of the present invention are one or more p-substituted phenylazides or azidoindoles will be applied to the keratinaceous material from a coloring composition in which it is contained. The concentration of the p-substituted phenylazide component that will be contained in the composition will generally amount to from about 0.01% to about 12% by weight of the p-substituted phenylazide or azidoindole component based on the total weight of the coloring composition. In the preferred practice of this invention, this concentration will be about 0.1% to about 1% of the same weight basis.

The coloring composition that will be used in the practice of the process of this invention can also contain a so called color coupler or modifier component. Agents of this character are well known in the hair dye art and are characterized by the fact that by themselves they do not impart color to hair when applied to hair in presence of an oxidizing agent or when exposed to light source. However, when applied to hair together with a primary hair dye intermediate from the prior art, such as a p-phenylenediamine, they will react with that intermediate and color hair a different color than that which might be obtained by the oxidation dyeing with the primary hair dye intermediate itself.

Numbers of classes of color couplers are known in the prior art which are useful for optional use in accordance with the purposes of the present invention. One or more of these color couplers (hereinafter referred to as the color coupler component) can be employed in the practice of the present invention. By way of illustrating the classes of color couplers that may be used herein, mention may be made of the following well known classes of couplers: m-phenylenediamines, naphthols, phenols, m-aminophenols, pyrazolones, beta diketones, 4-alkoxy and 4,6-dialkoxy-1,3-phenylenediamines, and the likes.

More specifically illustrating some color couplers that can be employed in the preferred practice of this invention, mention can be made of 5-amino-o-cresol, m-aminophenol, m-phenylenediamines, resorcinol, alpha-naphthol, 2-methylresorcinol, and mixtures thereof.

In carrying out the process of this invention the phenylazide or azidoindole alone or together with one or more color couplers (i.e. the color coupler component) are applied to the keratinaceous material from a coloring composition that may also contain the color coupler component in conjunction with the p-substituted phenylazide or azidoindole component described above. Any further reference to a "phenlyazide" is meant also to include alternatively an azidoindole. The concentration of color coupler component contained in the coloring composition may vary over a range depending on the selected coupler component, the phenylazide component utilized, the results desired and other such consideration. Usually the concentration of the color coupler component in the coloring composition will be in the range of from about 0.01% to about 55% by weight based on the total weight of said coloring composition, with the preferred range being from about 0.01% to about 3% on the same weight basis. The selection of a suitable coupler or couplers can be accomplished by routine experimentation by a hair dye formulator with average skill in the art.

The coloring composition utilized for the present purposes can take any of a variety of forms. Thus, it can be a simple solution or suspension of the phenylazide component and of the optional color coupler component in a liquid vehicle of which water will usually be the major component. However, other vehicles for applying the color agents employed herein are well known to those skilled in this art. For example, the coloring composition can take the form of a lotion, gel or aerosol composition.

Depending upon the form of the coloring composition, the results desired or organoleptic requirements other hair coloring adjuvants may be incorporated in the coloring composition. These include such items as solvents, surfactants, buffers, stabilizing agents and thickeners.

The pH of the coloring compositions used in the present process will generally be on the alkaline side. Usually, this will be in the range of pH from about 7 to about 12 with the preferred pH being from about 8 to about 10. In some case acid pH is more useful. For example, 5-azidoindole gives a more intense color at pH 6.

In the carrying out the process of the present invention, the keratinaceous material is contacted with the coloring components described above. The specific amount employed is not critical. The means of application and the amounts used generally correspond to the treatment of keratinaceous material with other customary treatment materials. In a typical case, in coloring hair, from about 1 to 5 ml of coloring composition solution per gram of hair can be employed.

The time period during which the keratinaceous material remains in contact with the coloring composition to permit it to absorb sufficient coloring composition may vary. This generally will be in the range of from about 5 minutes to about 2 hours, and preferably from about 10 minutes to about 45 minutes.

Following the application of the coloring composition and the exposure of the treated keratinaceous material to a suitable light source it is preferable to remove excess color composition. This will usually be done by rinsing the treated keratinaceous material with water. Alternatively, the rinsing or wiping step might be carried out prior to exposure of the treated material to a suitable light source.

Usually, direct or indirect sunlight will be used as the light source but, of course, artificial or other suitable light source can be determined by routine experimentation. The time of exposure to the light can also vary. Generally this will be in the range of from about 5 minutes to about 60 minutes. In the preferred cases this range will be from about 10 minutes to about 45 minutes. The obtention of maximum color intensity requires somewhat longer exposure, however desirable shades can also be obtained within shorter times of application.

The following examples are given to further illustrate this invention. It is to be understood, however, that the invention is not limited thereto.

The following are some typical examples of compositions that may be used in the practice of the present invention.

EXAMPLE 1

About 2 gm of bleached hair was placed in an aqueous p-aminophenylazide solution (0.2%) at pH 9.5. After being exposed to sunlight for 20 minutes, the swatch was shampooed and dried to give dark brown shade.

EXAMPLE 2 p-Aminophenylazide hydrochloride salt (17 mg) and 5-amino-o-cresol (13 mg) was dissolved in 9 ml of 95% ethanol and 9 ml of aqueous Carbopol 940 solution (0.75% w/w). The pH was adjusted to 9.5 with 2-aminoethanol. Approximately 2 g. bleached hair was placed in the solution. After exposure to direct sunlight for 20 minutes, followed by shampooing and rinsing under tap water, the hair acquired a magenta shade. Same result was obtained when a sunlamp was employed as the light source.

EXAMPLE 3

An aqueous solution of 5-azidoindole (0.2%) at pH 6.5 was used to treat about 2 g bleached hair under direct sunlight for 30 minutes. The hair was reddish brown after shampooing.

EXAMPLE 4

Potassium 4-azidophenoxide (0.08 mg), 5-amino-o-cresol (0.072 mg) and 95% ethanol (1.0 g) were added to an aqueous solution of polyquaternium-10 (0.88%) to give a total of 10 g. This solution was used to treat 2 g of blended gray hair for 30 minutes. After being rinsed and dried the hair was then placed by the window under indirect sunlight. A reddish brown shade developed gradually and reached maximum intensity in about 2 to 3 days.

EXAMPLE 5

4-Azido-2-nitrophenol (15.5 mg), alpha-naphthol (20 mg), 95% ethanol (2.5 g) and water (7.5 g) were mixed, and the pH of the solution was adjusted to 9.5. This solution was used to treat blended gray hair for 30 min. The hair was then rinsed and dried. When exposed to indirect sunlight, an orange brown shade was obtained on the swatch and on the finger skin of the operator.

EXAMPLE 6

A solution containing 10 mg of p-azidoanisole, 20 mg of alpha-naphthol, 2.5 g of 95% ethanol, and 7.5 g of water at pH 9.5 was used to treat commercially bleached hair for 30 min. The hair swatch was then rinsed and exposed to indirect sunlight. An apricot color was developed over a period of 2 to 3 days.

EXAMPLE 7 p-2-Hydroxyethoxyphenylazide (14 mg), alpha-naphthol (20 mg) were both dissolved in 2.5 g of 95% ethanol and 7.5 g of water. After adjusting the pH to 9.5 with monoethanolamine, the solution was used to treat the hair as described in Example 6 to give a reddish blond shade after exposure to indirect sunlight.

EXAMPLE 8

A pH 9 solution containing 0.17% (w/v) of p-aminophenylazide, 0.11% of resorcinol and, 20% ethanol was applied to the surface of the forearm for 5 mins. No color development was apparent until the treated area was exposed to sunlight. A brownish color resulted on the hair and forearm of the operator that was not removable by shampoo.

EXAMPLE 9

Resorcinol (0.1 g), alpha-naphthol (0.025 g), p-hydroxyphenylazide (0.1 g) and p-aminophenylazide (0.1 g) were dissolved in 95% ethanol (5 g) and 30 g aqueous solution of cocoamphocarboxypropionate (5% w/w) and polyquaternium 10 (1.5% w/w) with pH adjusted to about 9 by ethanolamine. No color was observed on the gray hair (2 g) after treated with this solution for 30 minutes and rinsed with tap water. A brown shade was obtained in the swatch after exposing the swatch to indirect sunlight. It reached its maximum intensity in about two days.

EXAMPLE 10

Hair is dyed as in Example 1, except that the aromatic azide employed has the formula:

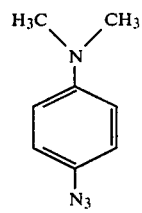

EXAMPLE 11

Hair is dyed as in Example 1, except that the aromatic azide is p-amino-m-chloro-phenylazide.

EXAMPLE 12

Hair is dyed in Example 1, except that the aromatic azide is 2-p-azido-anilino-ethanol.

EXAMPLE 13

A piece of wool (6.5 cm×15 cm) was placed in a pH 9 aqueous solution containing p-azidoanisole (0.04% by weight) and 5-amino-o-cresol (0.3% by weight). After being exposed to the sunlamp for 30 min., the swatch was rinsed. A reddish brown shade was obtained.

The following study was carried to test the effectiveness of the process of the present invention. The gram samples of commercially bleached hair was spread over an evaporation dish containing 10.0 ml of pH 9.0 buffer solution containing p-aminophenylazide (0.01 M) and various amounts of coupler set forth in Table I below. The buffering agents employed were boric acid/borax. The whole dish was immediately placed outdoors and exposed to direct sunlight for 20 min. The dyed swatch was shampooed and rinsed under tap water at ambient temperature. Various shades of color were obtained on swatches by employing different couplers or different combinations of couplers. Hunter tristimulus colorimeter readings of the hair tresses after one shampoo are also given in Table I.

TABLE I

| Hunter Readings of Swatches Dyed Photochemically* | | | | |
|---|---|---|---|---|
| Couplers Used | Coupler Concentration (M) | L | a | b |
| None | | 22.05 | 1.98 | 4.73 |
| 5-amino-o-cresol | 0.01 | 16.19 | 13.70 | 0.54 |
| m-aminophenol | 0.01 | 16.11 | 2.94 | 3.32 |
| m-phenylenediamine | 0.01 | 10.67 | 1.82 | −6.71 |
| resorcinol | 0.01 | 19.70 | 2.16 | 5.67 |
| resorcinol/m-phenylenediamine | 0.01/ 0.001 | 16.96 | −0.45 | −3.06 |
| resorcinal/alpha-naphtol | 0.01/sat. solution | 15.30 | 6.54 | −6.22 |
| *untreated sample of bleached hair | | 56.28 | −0.40 | 16.34 |

Table II gives the results of dyeouts using the conventional oxidation hair dyeing method with the identical liquor to hair ratio. The pH 9 dye solution contains 0.01 M of both p-phenylenedimaine and the given coupler, as well as 3% $H_2O_2$. The dyeing period is also 20 min. and each tress is shampooed and rinsed.

TABLE 11

| | Hunter colorimeter readings of swatches dyed with $H_2O_2$ as oxidant. | | |
|---|---|---|---|
| Coupler | L | a | b |
| resorcinol | 13.12 | 1.34 | 2.51 |
| m-phenylenediamine | 8.64 | 0.64 | −2.04 |
| m-aminophenol | 11.88 | 0.89 | 2.08 |

Comparison of the two tables shows that photodyeing with the phenylazide serves as good alternative to the conventional dyeing in which p-phenylenediamine and a large excess of $H_2O_2$ are used, even though the color intensity of the photodyed swatches is somewhat lower.

We claim:

1. A process for coloring keratinaceous material which comprises contacting said keratinaceous material with a coloring composition which contains an aromatic azide or azidoindole component having the formula

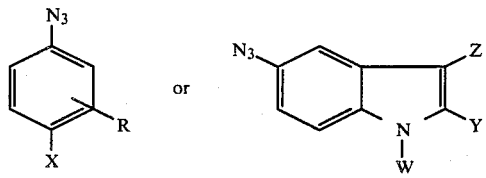

wherein X is hydroxyl, alkoxyl, NR′R″, in which R′ and R″ are independently of each other hydrogen, alkyl or hydroxyalkyl, and if R′ is H or alkyl, then R″ can be further carbamylalkyl, mesylaminoalkyl, acylaminoalkyl, sulfoalkyl, piperidinoalkyl or morpholinoalkyl, R′ and R″ can also form with the nitrogen atom to which they are attached, a piperidine or morpholine ring, R is hydrogen, alkyl, hydroxyalkyl, halogen, nitro, cyano or alkoxyl, W, Y and Z are independently of each other H or R′, wherein all of the aforementioned alkyl moieties can have between 1 and 8 carbon atoms, and then exposing the contacted keratinaceous material to a suitable light source for sufficient time to develop the color.

2. The process of claim 1 wherein the composition further comprises at least one color coupler component capable of interacting with said aromatic azide or azidoindole to color keratinaceous material.

3. The process of claim 1 in which the concentration of the aromatic azide or azidoindole in the composition is from about 0.01% to about 12% by weight, the pH of the composition is from about 7 to 12, and the exposure to the light is over a period of about 5 minutes to about 60 minutes.

4. The process of claim 2 in which the concentration of the aromatic azide or azidoindole in the composition is from about 0.01% to about 12% by weight, the pH of the composition is from about 7 to 12, and the exposure to the light is over a period of about 5 minutes to about 60 minutes.

5. The process of claim 4 wherein the concentration of the coupler is from about 0.01% to about 55% by weight.

6. The process of claim 1 in which the concentration of the aromatic azide or azidoindole in the composition is from about 0.01% to about 1% by weight, the pH of the composition is from about 8 to about 10, and the exposure to the lights is over a period of about 10 minutes to about 45 minutes.

7. The process of claim 2 in which the concentration of the aromatic azide or azidoindole in the composition is from about 0.01% to about 1% by weight, the pH of the composition is from about 8 to about 10, and the exposure to the lights is over a period of about 10 minutes to about 45 minutes.

8. The process of claim 7 wherein the concentration of the coupler is from about 0.1% to about 35% by weight.

9. The process of claim 2, wherein the color coupler component is at least one naphthol, phenol, m-phenylenediamine, m-aminophenol, pyrazolone or beta-diketone.

10. The process of claims 1 or 2, wherein the light source in sunlight, an artificial UV or visible light source.

11. The process of any one of claims 1 or 2, wherein the keratinaceous material contacted with said composition is wiped off or rinsed with water to remove excess composition prior to leaving exposed to said light source.

12. A process according to claim 1 wherein said keratinaceous material is selected from the group consisting of hair, wool and skin.

* * * * *